United States Patent [19]
Yu

[11] Patent Number: 5,789,255
[45] Date of Patent: Aug. 4, 1998

[54] BLOOD GLUCOSE STRIP HAVING REDUCED SENSITIVITY TO HEMATOCRIT

[75] Inventor: Yeung S. Yu, Pleasanton, Calif.

[73] Assignee: Lifescan, Inc., Milpitas, Calif.

[21] Appl. No.: 902,581

[22] Filed: Jul. 29, 1997

Related U.S. Application Data

[63] Continuation-in-part of Ser. No. 544,083, Oct. 17, 1995, abandoned.

[51] Int. Cl.[6] .................................................. C12Q 1/54
[52] U.S. Cl. ................................. 536/95; 422/56; 422/58
[58] Field of Search .................................. 422/56, 58, 61; 436/95

[56] References Cited

U.S. PATENT DOCUMENTS 5,306,623  4/1994  Kiser et al. .................................. 435/14

Primary Examiner—Lyle A. Alexander
Attorney, Agent, or Firm—James Riesenfeld

[57] ABSTRACT

A reagent strip for measuring glucose concentration in whole blood has reduced interference of hematocrit with the glucose measurement. When a biological fluid contacts the strip, it causes, in a reagent impregnated in the strip, a color change that is a measure of the glucose concentration in the fluid. However, the color change is also affected by the red blood cell concentration (hematocrit), thereby reducing the accuracy of the glucose measurement. The hematocrit effect is reduced by adding to the reagent an acrylic acid polymer.

13 Claims, 3 Drawing Sheets

BLOOD GLUCOSE STRIP HAVING REDUCED SENSITIVITY TO HEMATOCRIT

CROSS REFERENCE TO RELATED APPLICATION

This application is a continuation-in-part of U.S. application Ser. No. 544,083, filed on Oct. 17, 1995, now abandoned.

FIELD OF THE INVENTION

This invention relates to a dry phase reagent strip for measuring glucose concentration in a sample of whole blood; more particularly, a strip that is relatively insensitive to the hematocrit of the blood sample.

BACKGROUND OF THE INVENTION

Dry phase reagent strips incorporating enzyme-based compositions are used extensively in clinical laboratories, physicians' offices, hospitals, and homes to test samples of biological fluids for glucose concentration. In fact, reagent strips have become an everyday necessity for many of the nation's several million diabetics. Since diabetes can cause dangerous anomalies in blood chemistry, it can contribute to vision loss, kidney failure, and other serious medical consequences. To minimize the risk of these consequences, most diabetics must test themselves periodically, then adjust their glucose concentration accordingly, for instance, through diet control and/or with insulin injections. Some patients must test their blood glucose concentration as often as four times or more daily.

It is especially important for diabetics who must control their diet in order to regulate sugar intake and/or administer insulin injections, and who must be guided this regard by frequent tests of blood glucose concentration, to have rapid, inexpensive, and accurate reagent strips for glucose determination.

Reagent strips are known that contain an indicator which turns a different shade of color, depending on the concentration of glucose in a blood sample that has been applied to the strip. Some of these strips include an enzyme, such as glucose oxidase, which is capable of oxidizing glucose to gluconic acid lactone and hydrogen peroxide. They also contain an oxidizable dye and a substance having peroxidative activity, which is capable of selectively catalyzing oxidation of the oxidizable dye in the presence of hydrogen peroxide. (See, for example, U.S. Pat. No. 4,935,346, issued Jun. 19,1990, to Phillips et al.)

Whether the test is conducted in the home, physician's office, clinic, or hospital, accuracy and reproducibility of the glucose determination are extremely important. In the case of a color-indicating reagent strip, it is desirable that the color change be pronounced and be insensitive to variations in compounds contained in the blood other than glucose. In the case of a visually-read reagent strip, it is especially important that diabetics, who may be suffering from impaired vision, have a test reagent that exhibits a significant color change dependent upon glucose concentration. Color change, as exhibited by a change in absorbance and/or reflectance at a given wavelength, is also important for the accuracy of meter-read strips.

The performance of reagent strips may be affected by the presence of various interfering factors, and the need to reduce or eliminate the effect of interferents in clinical chemistry has been recognized by others. For example, Arter et al., EPO application No. 93111290.8, published on Jan. 19, 1994, disclose an analytical element for the determination of an analyte in an aqueous fluid. The element includes a reagent capable of binding free sulfhydryl groups present in the fluid. Arter et al. are primarily interested in detecting analytes such as acetaminophen, salicylate, creatinine, cholesterol, HDL cholesterol, triglycerides, glucose and uric acid. They use enzymes that produce hydrogen peroxide, which is assayed by way of peroxidase-coupled redox chemistry. The interfering sulfhydryl groups (such as N-acetyl cysteine, which appears in the serum of persons taking certain types of medication) may be present in the fluid and can trigger oxidation/reduction, even in the absence of the analyte. Arter et al. address the problem of the interfering free sulfhydryl groups by adding agents that react with and bind sulfhydryl groups. Suitable agents include maleimide, N-ethylmaleimide, iodoacetamide, silver nitrate, and gold chloride.

Ismail et al., U.S. Pat. No. 5,185,247, issued on Feb. 9, 1993, disclose an enzyme-based test strip that is stabilized by the addition of various compositions. They include imidazole among the agents that impart heat stability, but it is only effective if the strip is also impregnated with an "ascorbate interference composition," which includes mercuric oxide and sarcosine. Incorporating heavy-metal oxides in the reagent is generally undesirable, because they are toxic.

Matzinger et al., EPO application No. 93303643.6, published on Dec. 15, 1993, disclose a reagent strip for measuring the concentration of glucose in whole blood. The strip has a testing pad that contains a reagent system that changes color to indicate the glucose concentration-L The testing pad is formed from an anisotropic membrane, which has relatively large pores near one major surface and smaller pores near the opposite surface. A porous transport medium is attached to the large-pore surface of the pad. The whole blood sample is applied to the transport medium, which transfers a detectable portion of the sample to the large-pore side of the pad. Glucose in the sample then moves toward the opposite side, where it reacts with the reagent to cause a color change that is visible from the small-pore side of the pad and that indicates the glucose concentration in the sample.

Kiser et al., U.S. Pat. No. 5,306,623, disclose a blood glucose test strip that includes a separation matrix for separating red blood cells from whole blood. A test reagent reacts with the separated component to cause a color change that indicates the glucose concentration in the blood. Among the components that are disclosed for inclusion in a separation layer are polyacrylic polymers (CARBOPOL®). While these "separation components" (also referred to as "hematocrit adjusting agents," without further explanation) are generally in a separate separation layer, Kiser et al. also disclose a single layer matrix that contains reagent which includes both signal production components and blood separation components. In any case, when specified, the separation components are included in amounts ranging from 7% to 35% w/v. In practice, CARBOPOL cannot be used in that concentration range in these reagents.

It is known that interfering factors can affect the color change of reagent strips that measure blood glucose. For example, reduced color changes in glucose determinations seem to correlate generally with the concentration of red blood cells in the blood (the hematocrit).

There is a need for a reagent strip that provides a pronounced change in color along a glucose-concentration continuum when exposed to blood containing glucose, Ideally, a reagent strip should provide accurate glucose concentrations over a range of about 50 to 400 mg/dL, even though exposed to whole blood samples having hematocrit levels that vary over the range of about 25% to 60% hematocrit.

SUMMARY OF THE INVENTION

In accordance with the present invention, a reagent strip for measuring glucose concentration in a sample of whole blood that contains red cells comprises (a) an anisotropic membrane having a sample side with relatively large pores and a testing side with relatively smaller pores, the membrane being adapted to accept the sample on the sample side and pass it toward the testing side; and (b) a testing reagent impregnated in the membrane, the testing reagent comprising (i) a component for creating hydrogen peroxide from glucose and oxygen;

(ii) an indicator for reacting with the hydrogen peroxide to cause a change in the color of the indicator; and (iii) an acrylic acid polymer, of molecular weight at least about 750,000, whose concentration is in a range from about 0.1% to about 2% w/v, whereby any effect of the red blood cells on the glucose concentration measurement is reduced by the acrylic acid polymer.

In a method of the present invention, a method for measuring glucose concentration in a sample of whole blood that contains red blood cells comprises the steps of:

(a) providing an anisotropic membrane, which (i) has a sample side having relatively large pores and a testing side having relatively smaller pores and (ii) is impregnated with a testing reagent that can react with glucose to cause a change in color of the testing side, the reagent comprising glucose oxidase, a peroxidase, an oxidizable dye or dye couple, and an acrylic acid polymer, of molecular weight at least about 750,000, whose concentration is in a range from about 0.1% to about 2% w/v;

(b) applying the blood to the sample side of the membrane; and (c) measuring the change in color of the testing side to determine the glucose concentration in the blood.

A reagent strip of the present invention provides a relatively simple, rapid determination of glucose concentration in an unmeasured sample of blood over a range of glucose concentrations. The reagent strip yields substantially constant values of glucose concentration for whole blood samples that have hematocrit levels in the range of about 25% to 60% hematocrit.

The strip is adapted to accept a sample of whole blood, containing red cells and glucose, applied onto the sample side. The sample volume need neither be determined nor, within reasonable limits, controlled. The porosity of the membrane permits fluid to pass from the sample side toward the testing side, for example by capillary action. Thus, the testing reagent can react with glucose in the blood to cause a color change on or near the testing side. The change in color depends on the concentration of glucose in the sample. The glucose concentration in the blood can be determined in a variety of ways; for example, by comparing the color of the testing side with a calibrated reference or a color chart; by reflectance photometry; or by having a series of segments that correspond to a range of glucose concentrations and determining the glucose concentration by noting the last segment that changes color within a particular time frame. The strongly-colored red cells, which would make it harder to detect the color change, are filtered out near the sample side of the anisotropic membrane, which is graduated from large pores on the sample side to smaller pores on the testing side. A variety of materials may be used for the various components of the reagent strip of this invention. Some of these materials are disclosed in U.S. Pat. Nos. 5,306,623, and 5,418,142, issued Apr. 26, 1994 and May 23, 1995, respectively, to Kiser, et al., and incorporated herein by reference.

The testing reagent comprises a component, such as glucose oxidase, for converting glucose to hydrogen peroxide and one or more components for detecting the hydrogen peroxide produced from the glucose present in the sample. The component for detecting hydrogen peroxide may be a peroxidase, preferably horseradish peroxidase, together with an "indicator" that changes color in the course of the reaction. The indicator may be an oxidizable dye or a dye couple. The peroxidase catalyzes the oxidation of the indicator in the presence of hydrogen peroxide.

The testing reagent further comprises an acrylic acid polymer that reduces the effect that variations in hematocrit (percentage of red blood cells in the whole blood sample) cause in the measured glucose concentration.

The test strip and method of the present invention permit measurements of glucose concentrations in blood samples having a glucose concentration in the range of about 50 to 400 milligrams per deciliter and a hematocrit level in the range of about 25% to 60%.

DETAILED DESCRIPTION OF THE INVENTION

Figure 1:
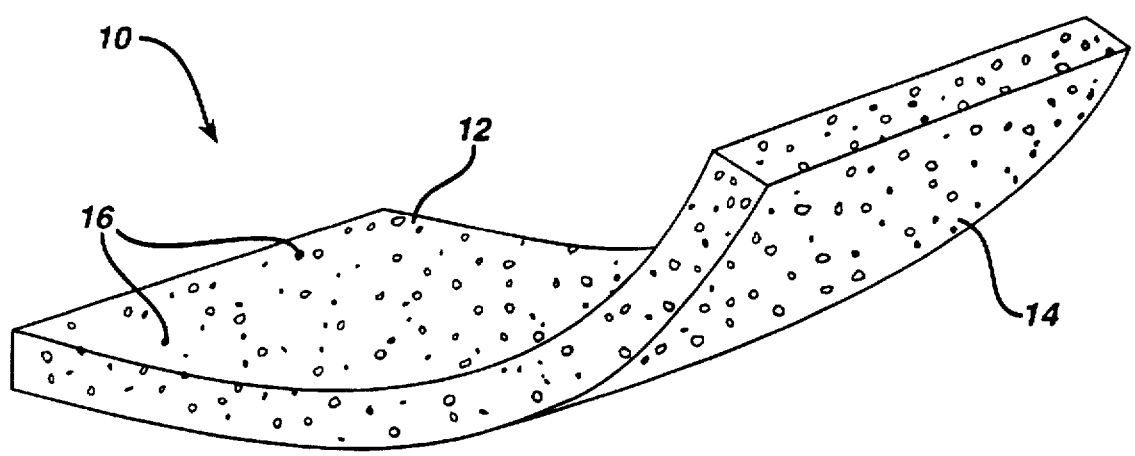
FIG. 1 is a perspective view of the membrane of a reagent strip of the present invention.

The present invention is a dry phase reagent test strip for measuring the concentration of blood glucose in whole blood. The key element of such a strip is a porous membrane that incorporates a testing reagent. The strip undergoes a color change in response to glucose in the blood sample that is applied to the strip. The membrane may be of a uniform composition or may be a coated substrate. It has a sample side, to which the sample is applied, and a testing side, where the color change is observed. Preferably, the membrane is anisotropic; more preferably, having a broad range of pore sizes. For example, a gradient of pore sizes in which the ratio of largest-to-smallest pores is in the range of about 100–400. On the side of the membrane where the pores are smallest, the void volume is relatively small, and the material of the membrane is generally quite dense, within a layer that can typically constitute up to 20% of the membrane's thickness. Within this layer, pore size is preferably in the range from about 0.1 to about 0.8 micrometers, with a nominal pore size preferably about 0.3–0.4 micrometers. On the large-pore side, pore size is preferably in the range from about 40 micrometers to about 125 micrometers. When the blood is applied to the sample (large pore) side, the sample encounters increasingly smaller pores as it penetrates the membrane. Eventually, solids such as red blood cells reach a position in the membrane where they can penetrate no further. The balance of the sample, still containing the dissolved glucose, penetrates through to the testing side. The anisotropic nature of the membrane permits relatively rapid flow rates through the membrane, even while filtration of the solids is taking place.

As the sample passes through the membrane, reaction with the reagent causes a light-absorbing dye to be formed or bleached in the void volume near the testing side, thereby substantially affecting reflectance from the membrane.

Polysulfones and polyamides (nylons) are examples of suitable membrane materials. Other polymers having comparable properties may also be used. The polymers may be modified to introduce other functional groups which provide for charged structures, so that the surfaces of the membrane may be neutral, positive, or negative.

A preferred method of preparing the porous material that forms the membrane is to cast the polymer without a supporting core. Such a membrane is, for example, the anisotropic polysulfone membrane available from Memtec, Inc., Timonium, MD. A membrane of less than about 200 micrometers thickness is usually employed, with about 115 to 155 micrometers being preferred. A thickness of about 130 to 140 micrometers is most preferred, particularly when the membrane is nylon or anisotropic polysulfone.

The membrane may be treated with testing reagent by dipping it into a mixture of the components, thereby saturating the membrane. Preferably, at least some of the components are applied to the membrane sequentially. Excess reagent may be removed by mechanical means such as, for example, an air knife, doctor blade, or glass rod. The membrane is then dried. Reagent tends to concentrate near the small-pore (testing) side of the membrane.

The testing reagent comprises (i) a component for converting glucose to hydrogen peroxide, (ii) a component for detecting hydrogen peroxide, and (iii) a component for reducing the effect of blood sample hematocrit level on the measured glucose concentration. The reagent may optionally further comprise a separating component which causes solids, such as red blood cells, to become attached to or entrapped in the membrane, effectively removing the solids from the biological fluid. Additional components may also be included as described hereinbelow and in the Examples.

Preferred components for converting glucose to hydrogen peroxide include glucose oxidase, an enzyme that is usually obtained from Aspergillus niger or Penicillium. Glucose oxidase reacts with glucose and oxygen to produce gluconolactone and hydrogen peroxide. Optimum glucose oxidase concentration depends on the composition of the indicator system. For example, if the indicator system is MBTHSB-ANS (which is described below), then glucose oxidase in the range from about 500–10,000 U/mL are suitable, more preferably from about 700–2000 U/mL, and most preferably about 1000 U/mL. Generally, higher concentrations of glucose oxidase cause the reaction to proceed more rapidly and inversely.

The hydrogen peroxide so produced reacts with the component for detecting hydrogen peroxide, which comprises a peroxidase that selectively catalyzes a reaction between the hydrogen peroxide and an indicator. The peroxidase uses hydrogen peroxide as an oxidant which is capable of removing hydrogen atoms from various substrates. A suitable peroxidase may contain ferriprotoporphyrin, a red hemin obtained from plants. Peroxidases obtained from animals, for example from the thyroid glands of animals, are also suitable. Horseradish peroxidase is especially preferred as a constituent of the component for detecting hydrogen peroxide.

The hydrogen peroxide, preferably catalyzed by a peroxidase, reacts either directly or indirectly to form or decompose an indicator dye that absorbs light in a predetermined wavelength range. Preferably the indicator dye absorbs strongly at a wavelength different from that at which the sample or the testing reagent absorbs strongly. The oxidized form of the indicator may be the colored, faintly-colored, or colorless final product that evidences a change in color of the testing side of the membrane. That is to say, the testing reagent can indicate the presence of glucose in a sample by a colored area being bleached or, alternatively, by a colorless area developing color.

Indicators that are useful in the present invention include both one- and two-component chromogenic substrates. One-component systems include aromatic amines, aromatic alcohols, azines, and benzidines, such as tetramethyl benzidine-HCl. Suitable two-component systems include those in which one component is MBTH, an MBTH derivative (see for example those disclosed in U.S. patent application Ser. No. 08/302,575, incorporated herein by reference), or 4-aminoantipyrine and the other component is an aromatic amine, aromatic alcohol, conjugated amine, conjugated alcohol or aromatic or aliphatic aldehyde. Exemplary two-component systems are 3-methyl-2-benzothiazolinone hydrazone hydrochloride (MBTH) combined with 3-dimethylaminobenzoic acid (DMAB); MBTH combined with 3,5-dichloro-2-hydroxybenzene-sulfonic acid (DCHBS); and [3-methyl-2-benzothiazolinone hydrazone] N-sulfonyl benzenesulfonate monosodium (MBTHSB) combined with 8-anilino-1 naphthalene sulfonic acid ammonium (ANS). MBTHSB-ANS is preferred.

The component for reducing the effect of blood sample hematocrit on the glucose measurement is an acrylic acid polymer (—CH2CH—COOH)$_n$. Such polymers are commonly known by the trademark CARBOPOL. Preferably, the molecular weight of the polymer is at least about 750,000. Most preferred is a molecular weight of about 750,000. The preferred concentration is in the range from about 0.1–2.0% w/v, with about 0.5% most preferred.

It is especially preferred that the method of this invention be practiced with a biological fluid having glucose concentration in the range of about 50 to 400 mg/dL. The method of the present invention demonstrates a greater consistency in color change per unit of glucose concentration in the sample than do conventional reagent strips, when employed within the preferred range of glucose concentration, particularly when hematocrit levels are in the preferred range —25–60%. The beneficial effect is greater at higher glucose levels.

In a preferred embodiment of a reagent strip of this invention, the reagent includes an inhibitor for inhibiting the color-changing reaction. In that embodiment, the testing reagent that is coated on or impregnated into the membrane is not uniform over the surface of the test strip. Instead, the reagent is preferably applied to the membrane in a series of parallel stripes, or "result segments", in which the composition in adjoining result segments increases, stepwise, in inhibitor concentration. Thus each succeeding segment requires, stepwise, a greater glucose concentration in the sample to cause the segment to change color. A strip of this design is "direct reading"; i.e., it provides direct quantitative visual readout. Details of this embodiment appear in copending U.S. patent application Ser. No. 411,238, filed on Mar. 27,1995, and incorporated herein by reference.

In another embodiment of the present invention, the reagent does not include inhibitor, but the strip does include, in addition to the reagent-impregnated membrane, a second-layer - a porous transport medium attached to the sample side of the membrane. In this "double-layer" embodiment, the transport medium is adapted to accept a whole blood sample and transport a detectable portion of the sample to the sample receiving surface of the membrane. The sample may be moved by capillary action. The transport medium preferably extends past one or more ends of the testing pad so as to form a reservoir for holding excess amounts of blood sample. Accordingly, it is preferred that the transport medium be capable of holding from about 10 to about 50 microliters of blood, preferably about 35 microliters of blood and of passing from about 3 to about 10 microliters of blood to the membrane. The transport medium may be composed of natural fibers, such as cotton or paper, as well as polyesters, polyamides, polyethylene, and other synthetic polymers. Polyethylene is the preferred transport medium material; for example, porous polyethylene available from the Porex Corp. of Fairburn, Ga. Optionally, this embodiment of the reagent strip may include a support layer, attached to the testing side of the membrane and having an aperture through which the color change can be measured. The color change on the testing side of the membrane is preferably measured by an optical sensor to yield the blood glucose concentration.

When the measurement is made by an optical sensor (i.e., by reflectance photometry), one or more calibrated reference color guides are exposed to a light source before or after the test side is exposed to the light source. For example, light may be sequentially reflected to a sensor from the color guide and the test side.

The sensor generates a signal that changes as the reference and the testing side are sequentially exposed to the light source. The changes in signal are then quantitatively related to concentration levels of glucose in the sample according to mathematical formulas which have previously been prepared using similar viewing means and samples of known glucose concentration. Details of this embodiment appear in copending U.S. patent application Ser. No. 493,435, filed on Jun. 22, 1995, and incorporated herein by reference.

The invention will now be described further with reference to the Figures. FIG. 1 shows a membrane 10 of the present invention for measuring the amount of glucose in a sample of whole blood. Although shown in an arched position, membrane 10 is flexible and is generally in a flat plane when used. The membrane includes a sample side 12, to which the blood sample is applied, and a testing side 14, on or near which a change in color indicates the presence of the glucose. The color change results from the interaction of the glucose with reagent impregnated in pores 16.

Preferably, pore sizes are relatively large near sample side 12 and decrease in size as testing side 14 is approached. The pore size gradient serves to trap red blood cells near sample side 12, so that their color does not interfere as much with the ability to see the color change that indicates the presence of the glucose.

Figure 2:
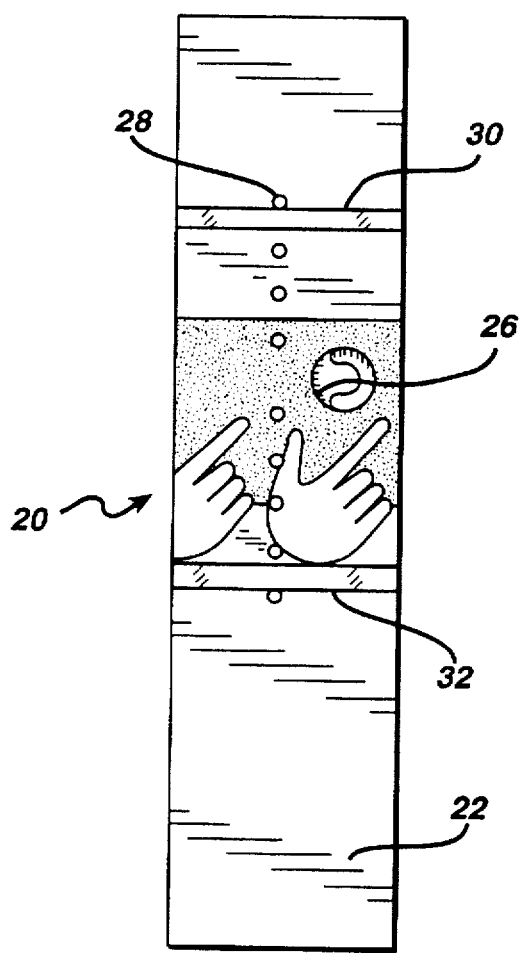
FIG. 2 is a plan view of the sample side of a direct-reading reagent strip of the present invention.
Figure 3:
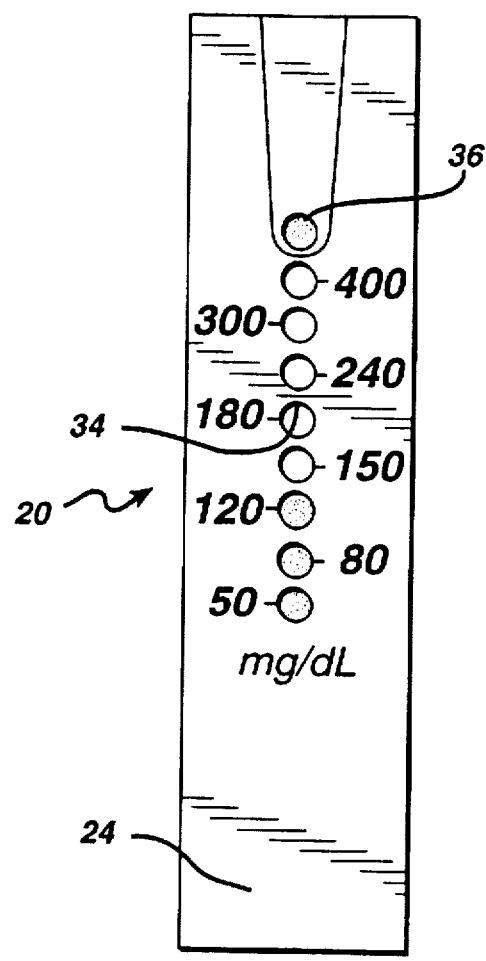
FIG. 3 is a plan view of the testing side of the strip of FIG. 2.

In a direct-reading test strip, the membrane of FIG. 1 is sandwiched between two cover sheets, which may be of any suitable thermoplastic film, well known in the art. FIGS. 2 and 3 are plan views of the sample side 22 and testing side 24 of a test strip 20, respectively. In use, a blood sample is applied to opening 26 on sample side 22. The sample spreads by capillary action longitudinally toward the top and bottom of the strip and permeates the membrane. Vent holes 28 facilitate sample flow into the strip. The appearance of sample through optional clear windows 30 and 32 confirms that sufficient sample has been provided for a measurement. Indicator circles, such as 34, on testing side 24 admit oxygen needed for the color-forming reaction and are labeled to show the blood glucose concentration. As the test progresses, indicator circles change color sequentially if the blood glucose concentration in the sample meets or exceeds the amount that corresponds to that circle. An optional chemical timer circle 36 indicates that adequate time has elapsed to read the strip. (Details concerning the timer appear in copending U.S. application Ser. No. 411,238, filed Mar. 27,1995.) The result depicted in FIG. 3 indicates that the sample glucose concentration is at least 120 mg/dL, but less than 150 mg/dL. Note that in FIG. 3 the color change caused by the reaction with glucose is from white to colored. However, the system could alternatively operate with an indicator dye that is destroyed by the glucose-induced oxidation, with a corresponding color change from colored to white.

Figure 4:
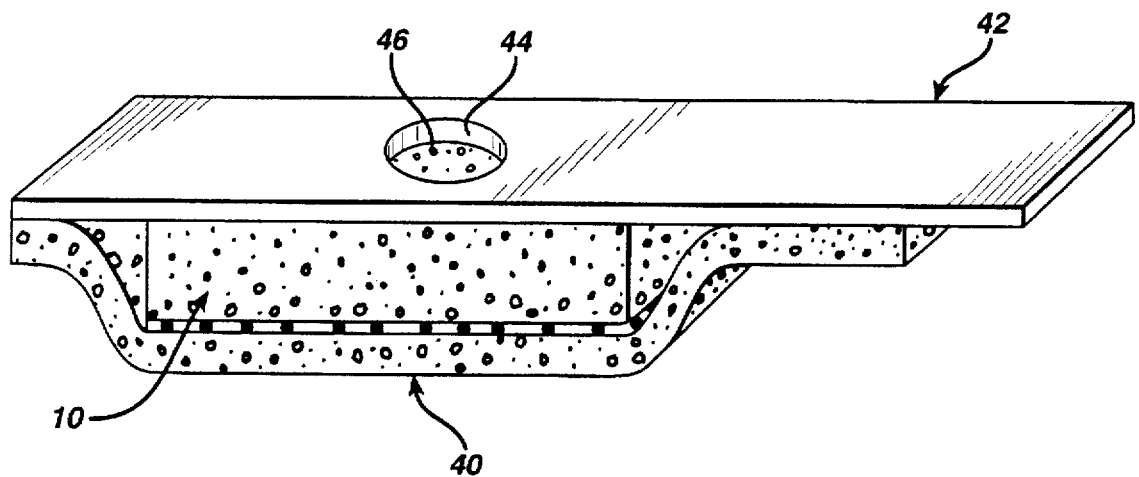
FIG. 4 is a perspective view of a double-layer reagent strip of the present invention.

FIG. 4 is a perspective view of a double-layer reagent strip in which the large-pore side of membrane 10 of FIG. I is adhered to transport medium 40. The small pore side is attached to optional support 42. Support 42 has an aperture 44 through which an optical sensor (not shown) can detect the color developed on testing surface 46 by the interaction of glucose in the blood sample with the reagent in membrane 10.

The following Examples demonstrate the effectiveness of acrylic acid polymer in reducing the sensitivity to variations in sample hematocrit level of a reagent strip in accordance with this invention. The Examples are not intended to be in any way limiting.

EXAMPLE 1

Several grades of polyacrylic acid were purchased from Aldrich Chemical, Milwaukee, Wis., and used without purification. CARBOPOL® 910 (polyacrylic acid, MW=750,000) purchased from BF Goodrich, Cleveland, Ohio, was used as a reference material. The polyacrylic acids from Aldrich and from BF Goodrich showed physical and chemical properties that are remarkably similar.

2.75 g of polyacrylic acid was suspended in 25 mL of acetonitrile and dispensed slowly into a stirring Enzyme Solution (Table 1). The resulting mixture was allowed to react for one hour, after which time the solution was adjusted with 75 mL of 0.1 M disodium citrate. The resulting yellow-brown solution (.46% w/v CARBOPOL) was coated onto a polysulfone membrane manufactured by Memtec. The coated membrane was dried in an air circulating oven at 56° C. for 10 minutes, during which time its color changed to a light yellow. The dried membrane was coated with a Dye Solution (Table 2) and was again dried as described above. The membrane was then cut into strips for blood testing.

TABLE 1

Enzyme Solution

| Component | Quantity |
|---|---|
| Water | 500 mL |
| Sodium Citrate | 6.96 g |
| Citric Acid | 5.64 g |
| EDTA, Disodium Salt | 0.42 g |
| Glucose Oxidase | 563,340 U |
| Horseradish Peroxidase | 506,160 U |
| Crotein SPA (a protein stabilizer, comprising hydrolyzed collagens, available from Croda, New York, NY) | 12 g |
| Gantrez S95 (a color fixing agent, comprising a polyvinyl acid, available from GAF, New York, NY) | 2.25 g |
| Mannitol | 5.00 g |

TABLE 2

Dye Solution

| Component | Quantity |
|---|---|
| meta [3-methyl 2-benzothiazolinone hydrazone] N-sulfonyl benzenesulfonate monosodium | 1.55 g |
| 8-Anilino-1-naphthalene sulfonic acid | 2.52 g |
| Denatured Ethanol | 280 mL |
| Water | 120 mL |
| Maphos 60A (a color enhancer, comprising an aliphatic phosphate ester, available from Mazer Chemicals, Gurnee, IL) | 3.68 g |

Strips prepared using polyacrylic acid of two different molecular weights, as well as CARBOPOL 910, were prepared and used to measure glucose concentration of whole blood, spiked with 400 mg/dL glucose, at three values of hematocrit —25%,43%, and 60%. Results appear in Table 3, together with results obtained with a control containing no polyacrylic acid.

TABLE 3

Hematocrit performance of 0.5% w/v polyacrylic acid-containing glucose test strips

| Case # | Polyacrylic acid | k/s* at 25% hema-tocrit | k/s* at 43% hema-tocrit | k/s* at 60% hema-tocrit | Ratio** of 25%/ 43% | Ratio** of 25%/ 60% |
|---|---|---|---|---|---|---|
| 1 | None | 8.26 | 7.85 | 5.37 | 1.05 | 1.54 |
| 2 | MW = 750,000 | 6.54 | 5.90 | 5.46 | 1.11 | 1.20 |
| 3 | MW = 1,250,000 | 5.56 | 5.52 | 5.21 | 1.01 | 1.07 |
| 4 | CARBOPOL 910 | 6.39 | 5.61 | 5.03 | 1.14 | 1.27 |

*k/s is a measure of color intensity
**ideal ratio is 1.00 (no hematocrit effect)

EXAMPLE 2

The procedure of Example 1 was repeated with compositions containing polyacrylic acids having a range of molecular weights, using a range of concentrations, including a control having no polyacrylic acid. To test the performance of strips that were prepared using the compositions, two sets of whole blood samples were used. Hematocrit levels were adjusted by recombining blood cells with plasma from the same donor and the glucose level was spiked to 395 mg/dL. One set of samples had 25% hematocrit and the other 60%. The results are shown in Table 4.

TABLE 4

Effects on hematocrit performance of polymer molecular weight and concentration

| Case # | Polyacrylic Acid | Mw | % w/v | Viscosity (cp) | k/s @ 25% hematocrit | k/s @ 60% hematocrit | Ratio 25%/60% |
|---|---|---|---|---|---|---|---|
| 1 | None (control) | | 0 | 2.6 | 9.43 | 6.02 | 1.57 |
| 2 | Aldrich (41,600-2) | 250,000 | 0.1 | 3.2 | 10.5 | 6.47 | 1.62 |
| 3 | Aldrich (41,600-2) | 250,000 | 1.5 | 7.4 | 9.97 | 6.49 | 1.54 |
| 4 | Aldrich (41,600-2) | 250,000 | 3.0 | 10.2 | 9.12 | 5.7 | 1.60 |
| 5 | Aldrich (41,600-2) | 250,000 | 4.0 | 14.3 | 9.1 | 4.95 | 1.84 |
| 6 | CARBOPOL 907 | 450,000 | 0.1 | 2.8 | 11 | 6.89 | 1.60 |
| 7 | CARBOPOL 907 | 450,000 | 1.0 | 10 | 10.6 | 4.97 | 2.13 |
| 8 | CARBOPOL 907 | 450,000 | 1.5 | 13 | 11.34 | 4.59 | 2.47 |
| 9 | CARBOPOL 907 | 450,000 | 2.5 | 33 | 11.85 | 4.96 | 2.39 |
| 10 | CARBOPOL 910 | 750,000 | 0.1 | 4 | 7.86 | 5.76 | 1.36 |
| 11 | CARBOPOL 910 | 750,000 | 0.5 | 27.5 | 6.9 | 5.76 | 1.20 |
| 12 | CARBOPOL 910 | 750,000 | 1.0 | 116 | 6.44 | 5.98 | 1.08 |
| 13 | CARBOPOL 910 | 750,000 | 1.5 | 208 | 6.02 | 5.79 | 1.04 |
| 14 | CARBOPOL 910 | 750,000 | 2.0 | >1000 | poor | poor | — |
| 15 | CARBOPOL 941 | 1,250,000 | 0.75 | 93 | 5.8 | 5.73 | 1.01 |
| 16 | CARBOPOL 934 | 3,000,000 | 0.5 | 8 | 5.7 | 5.02 | 1.14 |
| 17 | CARBOPOL 934 | 3,000,000 | 2.0 | 319 | 2.8 | 2.71 | 1.03 |
| 18 | CARBOPOL 940 | 4,000,000 | 0.1 | 3.5 | 7.98 | 5.56 | 1.44 |
| 19 | CARBOPOL 940 | 4,000,000 | 0.5 | 11.3 | 3.8 | 4.31 | 0.88 |
| 20 | CARBOPOL 940 | 4,000,000 | 1.0 | 110 | 3.38 | 3.75 | 0.90 |
| 21 | CARBOPOL 940 | 4,000,000 | 2.0 | 327 | 0.6 | 0.9 | 0.67 |

CARBOPOL is a trademark of BF Goodrich

The Examples demonstrate that the addition of polyacrylic acid can reduce the undesirable effect of hematocrit on measurements of glucose concentration in samples of whole blood. Several effects are at work. Generally, compositions containing a higher concentration of polyacrylic acid, or polymer of higher molecular weight, are more viscous, and reactions in these compositions are slower. Note, however, the exception that CARBOPOL 910 (MW=750,000) consistently yields more viscous solutions than does CARBOPOL 940 (MW=4,000,000). Perhaps due to steric hindrance, the highly cross-linked CARBOPOL 940 is less effective than the less cross-linked CARBOPOL 910 in interacting with proteins, such as the enzymes, in solution, resulting in a lower viscosity solution. High molecular weight polymer is less soluble, and the addition of high molecular weight and/or high concentrations of polymers also reduces color intensity (as measured by k/s—see U.S. Pat. No. 4,935,346). Thus, the optimum molecular weight and concentration involves compromises. Polymers of molecular weight at least about 750,000 and concentration in the range of about 0.1% w/v to about 2% w/v are preferred, with molecular weight in the range of 750,000 to 4,000,000 more preferred. The most preferred composition contains 0.5% w/v of 750,000 MW polymer.

It will be understood by those skilled in the art that the foregoing description and Examples are illustrative of practicing the present invention, but are in no way limiting. Variations of the detail presented herein may be made without departing from the scope and spirit of the present invention.

I claim:

1. A reagent strip for measuring glucose concentration in a sample of whole blood that contains red cells, comprising:
   (a) an anisotropic membrane having a sample side with relatively large pores and a testing side with relatively smaller pores, the membrane being adapted to accept the sample on the sample side and pass it toward the testing side; and
   (b) a testing reagent impregnated in the membrane, the testing reagent comprising
      (i) a component for creating hydrogen peroxide from glucose and oxygen,
      (ii) an indicator for reacting with the hydrogen peroxide to cause a change in the color of the indicator, and
      (iii) an acrylic acid polymer, of molecular weight at least about 750,000, whose concentration is in a range from about 0.1% to about 2% w/v,
   whereby any effect of the red blood cells on the glucose concentration measurement is reduced by the acrylic acid polymer.

2. The reagent strip of claim 1 further comprising a thermoplastic support for the membrane.

3. The reagent strip of claim 1 wherein the component for creating hydrogen peroxide from glucose and oxygen comprises glucose oxidase.

4. The reagent strip of claim 1 wherein the indicator comprises a peroxidase and a composition selected from the group consisting of (a) 3-methyl-2-benzothiazolinone hydrazone hydrochloride (MBTH) combined with 3-dimethylaminobenzoic acid (DMAB); (b) combined with 3,5-dichloro-2-hydroxybenzene-sulfonic acid (DCHBS); and (c) [3-methyl-2-benzothiazolinone hydrazone] N-sulfonyl benzenesulfonate monosodium (MBTHSB) combined with 8-anilino-1-naphthalene sulfonic acid ammonium (ANS).

5. The reagent strip of claim 4 wherein the indicator comprises a peroxidase and MBTHSB-ANS.

6. The reagent strip of claim 1 wherein the molecular weight of the acrylic acid polymer is in the range from about 750,000 to about 4,000,000.

7. The reagent strip of claim 1 wherein the molecular weight of the acrylic acid polymer is about 750,000.

8. The reagent strip of claim 1 wherein the concentration of acrylic acid polymer is about 0.5% w/v.

9. The reagent strip of claim 1 further comprising a porous transport layer attached to the sample side of the membrane for accepting the sample and passing a detectable portion of it to the sample side of the membrane.

10. The reagent strip of claim 1 wherein the testing reagent further comprises an inhibitor to inhibit the change in color of the indicator.

11. A method for measuring glucose concentration in a sample of whole blood that contains red blood cells, which comprises the steps of:
   (a) providing an anisotropic membrane, which
      (i) has a sample side having relatively large pores and a testing side having relatively smaller pores and
      (ii) is impregnated with a testing reagent that can react with glucose to cause a change in color of the testing side, the reagent comprising glucose oxidase, a peroxidase, an oxidizable dye or dye couple, and an acrylic acid polymer, of molecular weight at least about 750,000, whose concentration is in a range from about 0.1% to about 2% w/v;
   (b) applying the blood to the sample side of the membrane; and
   (c) measuring the change in color of the testing side to determine the glucose concentration in the blood.

12. The method of claim 11 wherein the glucose concentration in the blood is in the range from about 50 to about 400 mg/dL.

13. The method of claim 11 wherein the blood has a hematocrit level in the range from about 25% to about 60%.

* * * * *